US012151041B2

(12) United States Patent
Bergman et al.

(10) Patent No.: US 12,151,041 B2
(45) Date of Patent: Nov. 26, 2024

(54) CONDIMENT STERILIZATION DEVICES AND SYSTEMS

(71) Applicant: MSPLG of Florida, LLC, Lake Worth, FL (US)

(72) Inventors: Matthew Bergman, Lake Worth, FL (US); Kenneth Fagin, Gaithersburg, MD (US)

(73) Assignee: MSPLG of Florida, LLC, Lake Worth, FL (US)

( * ) Notice: Subject to any disclaimer, the term of this patent is extended or adjusted under 35 U.S.C. 154(b) by 0 days.

(21) Appl. No.: 18/393,996

(22) Filed: Dec. 22, 2023

(65) Prior Publication Data

US 2024/0207469 A1 Jun. 27, 2024

Related U.S. Application Data

(60) Provisional application No. 63/476,740, filed on Dec. 22, 2022.

(51) Int. Cl.
*A61L 2/10* (2006.01)
*A61L 2/24* (2006.01)
*A61L 2/26* (2006.01)

(52) U.S. Cl.
CPC .......... *A61L 2/10* (2013.01); *A61L 2/24* (2013.01); *A61L 2/26* (2013.01); *A61L 2202/11* (2013.01);
(Continued)

(58) Field of Classification Search
None
See application file for complete search history.

(56) References Cited

U.S. PATENT DOCUMENTS 6,461,568 B1 10/2002 Eckhardt
8,941,078 B2 * 1/2015 Tantillo ............... A63H 33/006
250/455.11
(Continued)

FOREIGN PATENT DOCUMENTS

AU 2021100602 A4 5/2021
CN 111494664 A 8/2020
(Continued)

OTHER PUBLICATIONS

International Search Report and Written Opinion mailed May 6, 2024 for International Patent Application No. PCT/US2023/085629.
(Continued)

*Primary Examiner* — Andrew Smyth
(74) *Attorney, Agent, or Firm* — Potomac Law Group, PLLC

(57) ABSTRACT

According to some embodiments, a condiment sterilizer can include: a base, a lid attached to the base and configured to move between an open position and a closed position, and a condiment tray mounted in the base. The base and the lid define an internal chamber when the lid is in the closed position. The condiment tray can include a center column, and one or more compartments disposed around the center column and configured to accommodate one or more condiment containers. The condiment sterilizer can further include at least one UV light device disposed on the center column and configured to emit UV light into the internal chamber. The condiment sterilizer can further include a controller configured to cause the lid to move from the closed position to the open position, and to raise the condiment tray, in response to a sensor sensing heat or motion.

19 Claims, 12 Drawing Sheets

(52) U.S. Cl.
CPC ..... *A61L 2202/122* (2013.01); *A61L 2202/14* (2013.01); *A61L 2202/23* (2013.01)

(56) References Cited

U.S. PATENT DOCUMENTS

| | | |
|---|---|---|
| 9,044,521 B2 | 6/2015 | Farren |
| 9,265,849 B2 | 2/2016 | Kerr |
| 11,116,857 B1 | 9/2021 | Benin et al. |
| 2006/0123800 A1 | 6/2006 | Metzner |
| 2007/0258851 A1 | 11/2007 | Fogg et al. |
| 2018/0110890 A1 | 4/2018 | Matsui |
| 2020/0353111 A1 | 11/2020 | Schmiddem et al. |
| 2020/0360549 A1 | 11/2020 | Neveu et al. |
| 2021/0177012 A1 | 6/2021 | White et al. |
| 2021/0308301 A1* | 10/2021 | Sperry ................. A61L 2/10 |
| 2021/0338865 A1 | 11/2021 | Lee et al. |
| 2021/0347705 A1 | 11/2021 | Goodman |
| 2022/0008583 A1 | 1/2022 | Garcia |

FOREIGN PATENT DOCUMENTS

| | | | |
|---|---|---|---|
| CN | 213698050 U | * | 7/2021 |
| KR | 200469022 | | 9/2013 |
| KR | 1020200002082 | | 1/2020 |
| KR | 102255658 | | 5/2021 |
| KR | 102316611 | | 10/2021 |
| KR | 20210134465 A | | 11/2021 |
| WO | 2020216979 A1 | | 10/2020 |

OTHER PUBLICATIONS

Unknown, "Fovero US Savitizing Box, UV Disinfection Box for Phone," website link: fovero—Indiamart.

Unknown, "Hyderabad DRDO lab develops Contactless Sanitisation Cabinet to sanitize phones, laptops," ANI News, 13 pages, (2020).

Unknown, "Samsung UV Sterilizer review: This wireless charger claims to kill coronavirus but utility is limited," India Today, 11 pages, (2020).

Unknown, "UV Based Disinfection Devices," Defense Research Development Organisation, Ministry of Defence, Government of India, 9 pages, (2022).

* cited by examiner

CONDIMENT STERILIZATION DEVICES AND SYSTEMS

CROSS-REFERENCE TO RELATED APPLICATIONS

This application claims the benefit of U.S. Provisional Application No. 63/476,740 filed on Dec. 22, 2022, the entire disclosure of which is incorporated herein by reference for all purposes.

BACKGROUND

1. Field

The disclosure relates to devices and systems for sterilizing containers. For example, the disclosure relates to devices and systems for sterilizing condiment containers.

2. Description of Related Art

It is common for restaurants, cafeterias, and food trucks to provide condiment containers, such as salt shakers, pepper shakers, ketchup bottles, mustard bottles, etc., in common areas and/or at dining tables. The condiment containers are typically handled by numerous people during a day. Thus, the condiment containers can become contaminated with pathogens, presenting a health hazard for restaurant patrons and employees.

It is important to routinely sterilize condiment containers in restaurants, cafeterias, and food trucks to promote a safe and clean dining or food service environment. Therefore, there is a need for improved devices for sterilizing condiment containers.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a condiment sterilizer can include: a base; a lid attached to the base and configured to move between an open position and a closed position; and a condiment tray mounted in the base. The base and the lid define an internal chamber when the lid is in the closed position. The condiment tray can include a center column, and one or more compartments disposed around the center column and configured to accommodate one or more condiment containers. The condiment sterilizer can further include at least one UV light device disposed on the center column and configured to emit UV light into the internal chamber.

In some embodiments, the condiment tray can be made of a UV-transmissive material.

In some embodiments, the condiment sterilizer can further include a reflective surface disposed on either one or both of the base and the lid.

In some embodiments, the at least one UV light device can include a plurality of UV light devices disposed on light strips that are attached to the center column at multiple locations spaced apart along a circumference of the center column.

In some embodiments, the condiment sterilizer can further include: a sensor configured to sense heat or motion; and a controller connected to the sensor and configured to cause the lid to move from the closed position to the open position in response to the sensor sensing the heat or the motion.

In some embodiments, the controller can be further configured to cause the condiment tray to move up in the base in response to the sensor sensing the heat or the motion.

In some embodiments, the condiment sterilizer can be further configured to cause the lid to move back to the closed position, cause the condiment tray to move down in the base, and turn on the at least one UV light device, in response to sensing a condiment container among the one more condiment containers being returned to the condiment tray.

In some embodiments, the controller can be further configured to cause the lid to move back to the closed position, and turn on the at least one UV light device, in response to sensing a condiment container among the one more condiment containers being returned to the condiment tray.

In some embodiments, the condiment sterilizer can further include at least one additional UV light device disposed on a bottom wall or a side wall of the base.

In another general aspect, a condiment sterilizer includes: a base; a lid attached to the base and configured to move between an open position and a closed position; and an inner tub disposed in the base. The inner tub can include a first hollow center column, and the inner tub and the lid can define an internal chamber when the lid is in the closed position. The condiment sterilizer can further include a condiment tray mounted over the inner tub in the internal chamber. The condiment tray can include a second hollow center column disposed over the first hollow center column, and one or more compartments disposed around the second hollow center column and configured to accommodate one or more condiment containers. The condiment sterilizer can further include a lift assembly mounted in the base and configured to raise and lower the condiment tray in the inner chamber. The inner tub can cover the lift assembly. The condiment sterilizer can further include at least one UV light device configured to emit UV light into the internal chamber.

In some embodiments, the lift assembly can include: a lead screw sleeve disposed in the first hollow center column; a lead screw disposed in the lead screw sleeve, the lead screw extending through an opening in a top wall of the first hollow center column and having a top end connected to the condiment tray; and a lift motor. The lift motor can be configured to: rotate the lead screw sleeve in a first direction relative to the lead screw and thereby cause the lead screw to move up and raise the condiment tray in the internal chamber, and rotate the lead screw sleeve in a second direction relative to the lead screw and thereby cause the lead screw to move down and lower the condiment tray in the internal chamber.

In some embodiments, the lift assembly can further include a stopper fixed to the lead screw. The stopper can be configured to: engage the top wall of the first hollow center column to limit upward travel of the condiment tray to a maximum height; and engage a ledge of the lead screw sleeve to limit downward travel of the condiment tray to a minimum height.

In some embodiments, the condiment sterilizer can further include a guide rail disposed on a side wall of the inner tub, and a guide channel disposed on a side wall of the condiment tray. The guide rail and the guide channel can be configured to engage each other to limit or prevent rotation of the condiment tray when the condiment tray is raised or lowered.

In some embodiments, the at least one UV light device includes one or more UV light devices disposed on the first hollow center column and the second hollow center column includes one or more open slots. When the condiment tray is disposed at a minimum height in the internal chamber, the second hollow center column can cover the first hollow center column and the one or more UV light devices can be exposed to the internal chamber by the one or more open slots.

In some embodiments, the condiment sterilizer can further include: a sensor configured to sense heat or motion; and a controller connected to the sensor and configured to control a motor of the lift assembly to raise the condiment tray in the internal chamber in response to the sensor sensing the heat or the motion.

In some embodiments, the condiment sterilizer can further include a lid drive assembly configured to move the lid. The controller can be further configured to cause the lid drive assembly to move the lid from the closed position to an open position in response to the sensor sensing the heat or the motion.

In some embodiments, the controller can be further configured to control the motor of the lift assembly to lower the condiment tray in the internal chamber, cause the lid drive assembly to move the lid back to the closed position, and turn on the at least one UV light device, in response to sensing a condiment container among the one more condiment containers being returned to the condiment tray.

In some embodiments, the controller can be further configured to control the motor of the lift assembly to lower the condiment tray in the internal chamber, and turn on the at least one UV light device, in response to sensing a condiment container among the one more condiment containers being returned to the condiment tray.

In some embodiments, the inner tub can further include a plurality of legs disposed on a bottom wall of the inner tub. The plurality of legs can support the inner tub on a bottom wall of the base such that a space for accommodating electronic components is formed between bottom wall of the inner tub and the bottom wall of the base.

Other features and aspects will be apparent from the following detailed description, the drawings, and the claims.

Figure 1:
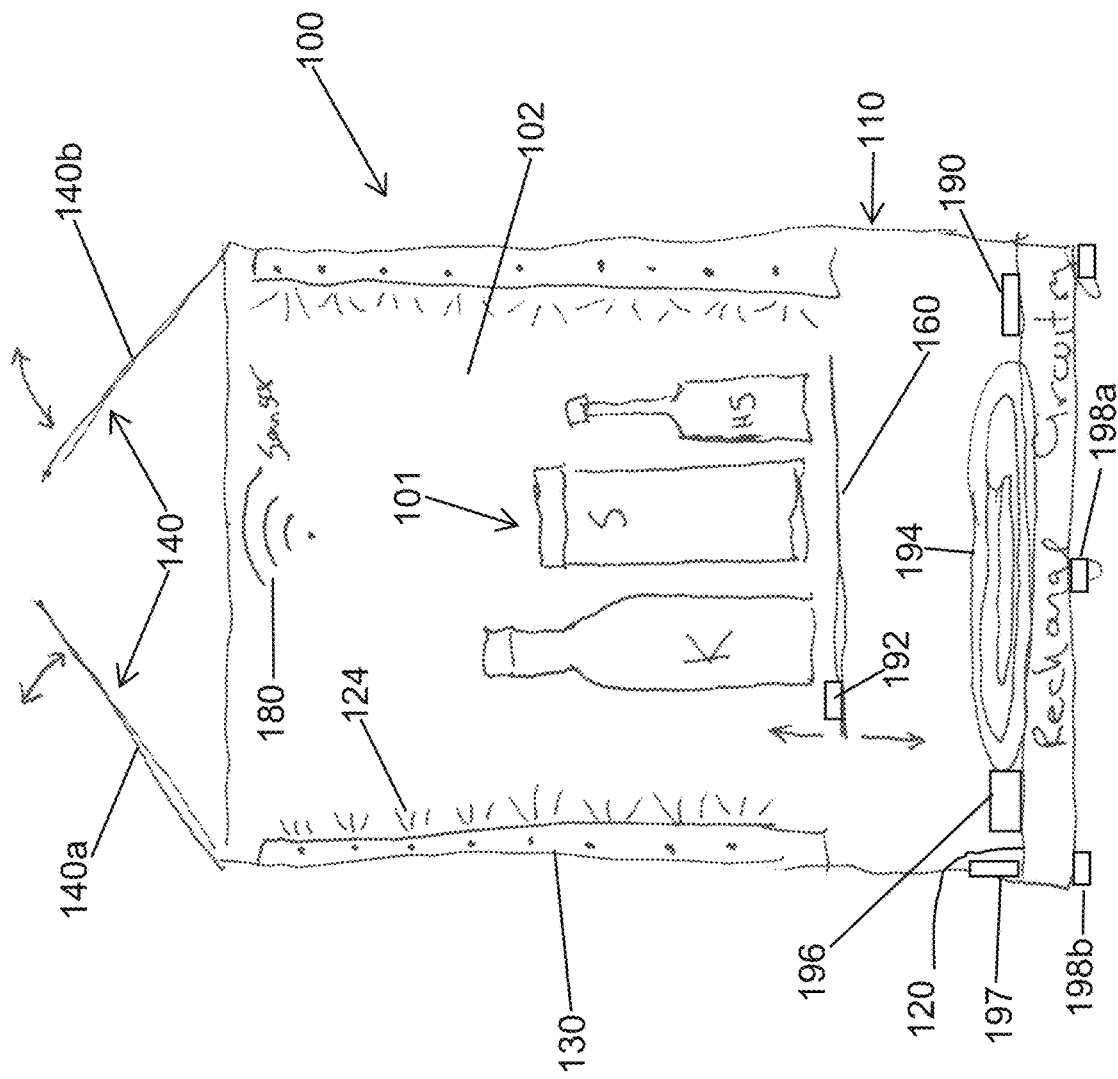
FIG. 1 is a cross-sectional view of a condiment sterilizer, according to an embodiment.

The features and aspects introduced here may be better understood by referring to the following Detailed Description in conjunction with the accompanying drawings, in which like reference numerals indicate identical or functionally similar elements. The drawings may not be to scale, and the relative size, proportions, and depiction of elements in the drawings may be exaggerated for clarity, illustration, and convenience.

DETAILED DESCRIPTION

The present disclosure is directed to devices and systems that use ultraviolet (UV) light to sterilize containers such as bottles and jars of condiments, salt and pepper shakers, etc., which are typically provided on a restaurant table and which may be handled by scores of people with unknown hygiene and/or illness status.

FIG. 1 illustrates a condiment sterilizer 100, according to an embodiment. As illustrated in FIG. 1, the condiment sterilizer 100 includes a base 110 and a lid 140 disposed at a top of the base 110. The lid 140 can include lid members or doors 140a and 140b that are pivotally attached to opposite sides of the base 110. Alternatively, in some embodiments, the lid members 140a and 140b can be replaced with a single lid member pivotally attached to one side of the base. An internal chamber 102 is disposed in the base 110, and is sized and configured to receive and contain a plurality of condiment containers 101 that are commonly provided at a restaurant table. For example, the condiment containers 101 can be bottles, jars, canisters, shakers, or the like, and can contain any of ketchup, mustard, steak sauce, hot sauce, salt, and pepper, for example. The condiment sterilizer 100 can sit on a table or counter of a restaurant, for example, with the condiment containers 101 held in the internal chamber 102. The lid 140 can be closed and opened to respectively close and open the internal chamber 102.

A moveable platform or tray 160 can be mounted to the base 110 and disposed in the internal chamber 102. The condiment containers 101 can be disposed on the movable platform 160. In some embodiments, the condiment containers 101 can be placed in a basket that sits on the platform, with the basket having conformal receptacles for each of the condiments to prevent one or more condiment containers 101 from toppling off the movable platform 160 as the movable platform 160 moves.

A plurality of UV light devices (e.g., UV-C LEDs or low wave UV light devices) 124 that do not harm human skin) that emit UV light having germicidal and/or or sanitizing properties are disposed in the internal chamber 102, and the internal chamber 102 can be internally reflective so that the internal chamber 102 will be filled with UV light when the UV light devices 124 are illuminated. For example, the UV light devices 124 can be disposed on an internal surface of a bottom wall 120 and/or one or more side walls 130 of the base 110.

The condiment sterilizer 100 can include a condiment delivery mechanism including, for example, a controller 190 and one or more motors and components connected thereto that can be operated by the controller 190 to open and close the lid 140, and to move the movable platform 160 up and down in the internal chamber 102.

A sensor 180, such as a motion sensor or a heat (e.g., IR) sensor, can be disposed on the outside of the condiment sterilizer 100 and operably connected to the controller 190 so that, when a person (e.g., a patron) wants condiments, the person can move their hand by the sensor 180 to activate the condiment delivery mechanism. That is, the controller 190 can activate the condiment delivery mechanism in response to detecting a signal generated by the sensor 180 movement of the hand or heat generated by the hand. This helps minimize the condiment sterilizer 100 itself becoming covered with pathogens. When the condiment delivery mechanism is activated, the controller 190, which is electrically connected to the light devices 124 to control turning the light devices 124 on an off, confirms that that the UV light devices 124 are off (e.g., not emitting light) or otherwise turns off the UV light devices 124, and then operates the one or more motors to open (e.g., pivot) the lid 140 (e.g., doors 140a and 140b) and raise the movable platform 160 within the internal chamber 102 to present the condiment containers 101 to the person so that the person can remove one or more condiment containers 101 from the movable platform 160. When the person has finished using the condiment container(s) 101 and places them back on the movable platform 160, the controller 190 can lower the movable platform 160 into the internal chamber 102. The UV light devices 124 can then be turned on by the controller 190 for a predetermined period of time to sanitize the condiment containers 101.

Various mechanisms can be used to cause the doors to swing open. For example, in some embodiments, the doors 140a and 140b can have arcuate toothed arms that are driven by a pinion gear attached to the output shaft of a small electric motor housed within the internal chamber 102. Various mechanisms can also be used to cause the movable platform 160 to rise from and descend back into the internal chamber 102. For example, electric motor-driven jack screws positioned at the corners of the internal chamber 102 (to keep the screws out of the way of the movable platform 160) can engage with drive nuts attached to the platform to move the platform up and down. Alternatively, electric motor-driven drive wheels (i.e., pinion gears) attached to the platform can engage with toothed tracks located along the side walls 130 of the internal chamber 102 to move the movable platform 160 up and down.

In one configuration, the person can cause the movable platform 160 and condiment containers 101 to descend back into the internal chamber 102 and the doors 140a and 140b to close by passing their hand in front of the sensor 180 while the doors 140a and 140b are open. That is, when the movement of the hand or heat from the hand is sensed by the sensor 180, the controller 190 can operate the condiment delivery mechanism to cause In another contemplated configuration, the controller 190 can cause the movable platform 160 and the condiment containers 101 to retreat back into the internal chamber 102 in response to detecting a weight of a condiment container 101 being returned to the platform (e.g., a change in a weight applied to the movable platform 160). For example, the controller 190 can detect the weight of the condiment container by sensing a slight voltage spike as the motor(s) of the condiment delivery mechanism work to keep the movable platform 160 in a given position, or by sensing a signal generated by a weight sensor 192 that is operably connected to the controller 190, and disposed on the movable platform 160 and configured to measure a weight applied to the movable platform 160.

As indicated above, the light devices 124 can be UV-C LEDs or low wave UV light devices that are not harmful to human skin. The UV light devices 124 are driven by electricity. Therefore, the condiment sterilizer 100 can have an electrical cord (not illustrated) to be plugged into an electrical outlet to provide power the UV light devices 124.

Because it is unlikely there would be an electrical outlet located by every table in a restaurant, however, the condiment sterilizer 100 can be rechargeable. To this end, the condiment sterilizer 100 can include one or more power-storage devices 194 such as rechargeable batteries, capacitors, etc., and corresponding recharging circuitry 196. In some embodiments, the recharging circuitry 196 can be configured for wireless recharging (e.g., Qi standard) such as that now present in many mobile devices, which utilizes charging coils in the device being charged and in the charger. Alternatively, the condiment sterilizer 100 can have a charging port 197 (e.g., for USB charging or charging using a pin-type plug) or, alternatively, exposed contacts on a bottom surface of the sterilizer. For example, the exposed contacts can include a center contact 198a can be located in the center of the bottom surface of the sterilizer and another, ring-shaped contact 198b can surround the center contact 198a. With such exposed contacts located on the bottom surface of the condiment sterilizer 100, the condiment sterilizer 100 can be recharged simply by setting it down on a charging pad with one (spring-biased) charging pin positioned to contact the center contact 198a and another (spring-biased) charging pin positioned to contact the ring-shaped contact 198b.

As described above, the condiment sterilizer 100 includes the doors 140a and 140b located at the top of the condiment sterilizer 100, and the movable platform 160 that moves vertically to present the condiment containers 101 to the person from the top of the condiment sterilizer 100 and to lower the condiment containers 101 back into the condiment sterilizer 100 for sanitizing. However, a condiment sterilizer according to the inventive concepts disclosed herein is not limited to such a configuration. For example, in other embodiments such as the embodiment of FIGS. 2A and 2B described below, a condiment sterilizer can have differently configured doors and a differently configured movable tray.

Figure 2B:
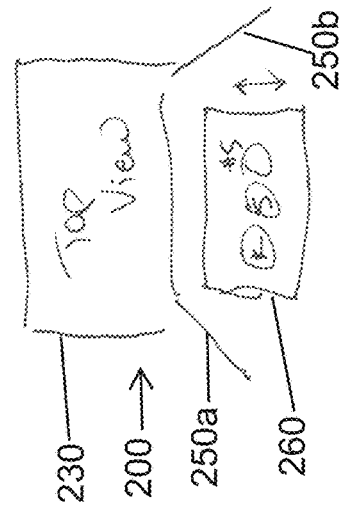
FIGS. 2A and 2B are cross-sectional and top views, respectively, of a condiment sterilizer, according to an embodiment.
Figure 2A:
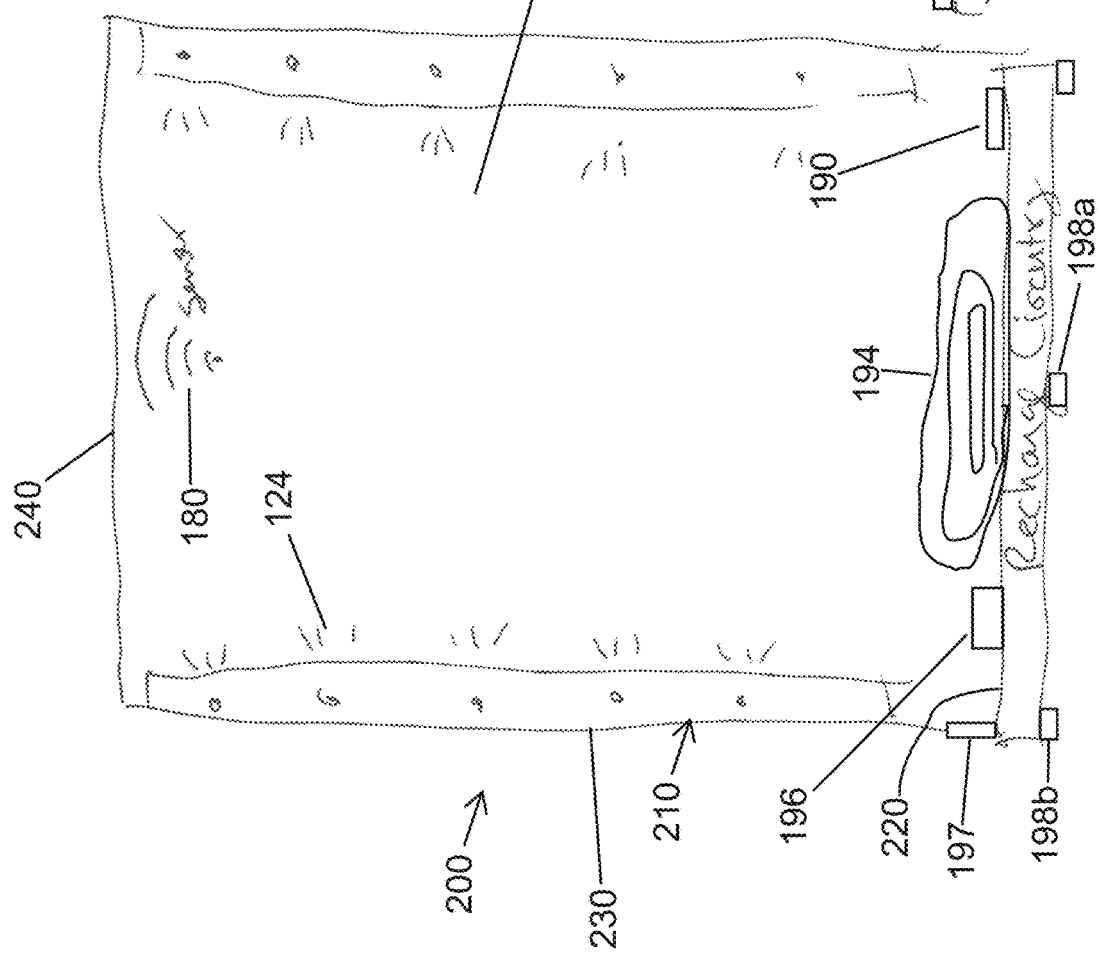

FIGS. 2A and 2B illustrate a condiment sterilizer 200, according to an embodiment. The condiment sterilizer 200 is similar to the condiment sterilizer 100 of FIG. 1, except that the condiment sterilizer 200 includes a base 210 having a bottom wall 220, and side walls 230, and a top wall 40 doors 250a and 250b (FIG. 2B) connected to the base 210 and disposed along a side portion of the condiment sterilizer 200, an internal chamber 202 disposed in the base 210, and a movable platform 260.

The doors 250a and 250b are pivotally attached to the base 210 and, when closed, form one side wall of the base 210. The doors 250a and 250b can be pivoted to open and close in any of the ways described above for the doors 140a and 140b of FIG. 1.

The movable platform 260 is configured to move into and out of the internal chamber 202 horizontally, similarly to the disc tray of a CD/DVD drive.

Figure 3:
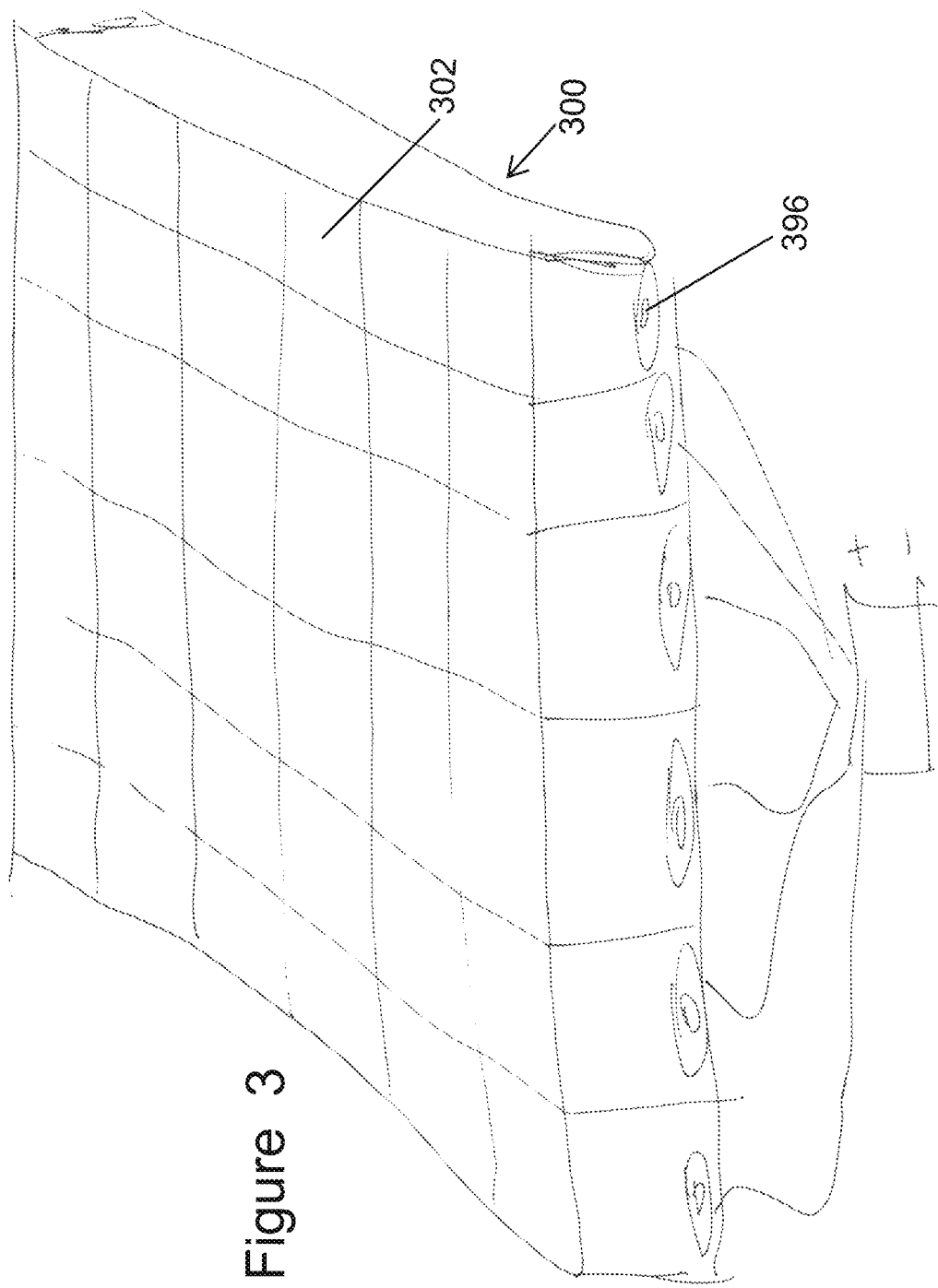
FIG. 3 illustrates a multiple-sterilizer rack, according to an embodiment.

To facilitate handling and recharging of multiple condiment sterilizer at the same time, a sanitizer system can include a multiple-sterilizer rack 300, as illustrated in FIG. 3. The rack 300 can be configured similarly to the type of racks frequently used in restaurants to transport and wash glasses. That is, the rack 300 can include multiple "cells" or compartments 302 (e.g., 36 cells, as illustrated in FIG. 3) that each can receive and recharge a single condiment sterilizer (e.g., condiment sterilizer 100/200). To recharge the condiment sterilizers, recharging circuitry 396 corresponding to the type of recharging hardware implemented in the condiment sterilizers—i.e., wireless charging coils or electrical contacts arranged to engage contacts on the bottoms of the sterilizers—is provided in the bottom of each cell 302. In embodiments in which the condiment sterilizer includes exposed charging contacts including a center recharging contact and an outer, surrounding charging contact as described above with respect to FIG. 1, then the condiment sterilizer can be placed within the cell in any angular or rotational orientation.

Figure 4:
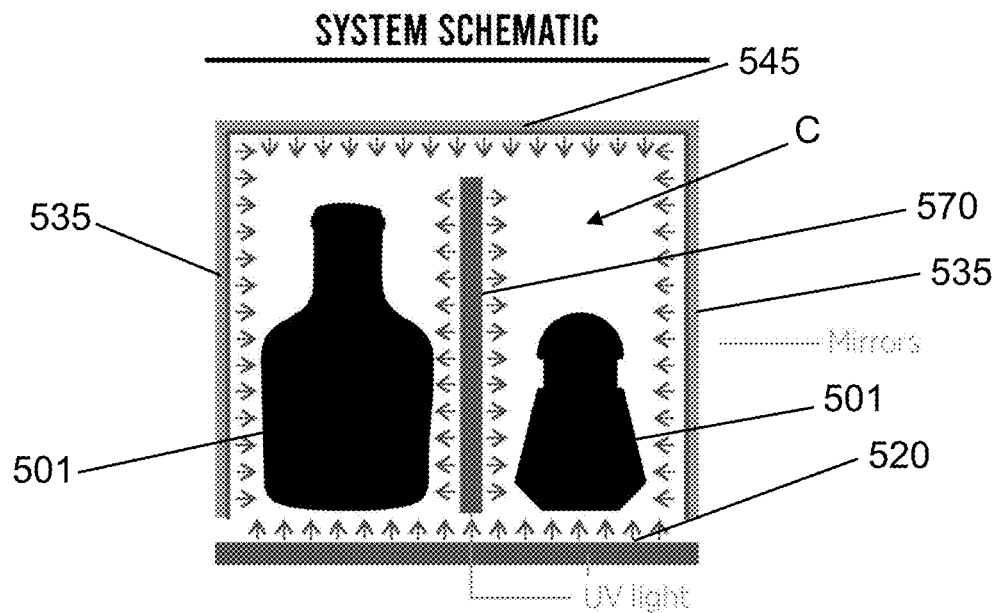
FIG. 4 is a schematic illustration of a cavity of a condiment sterilizer, according to an embodiment.
Figure 5:
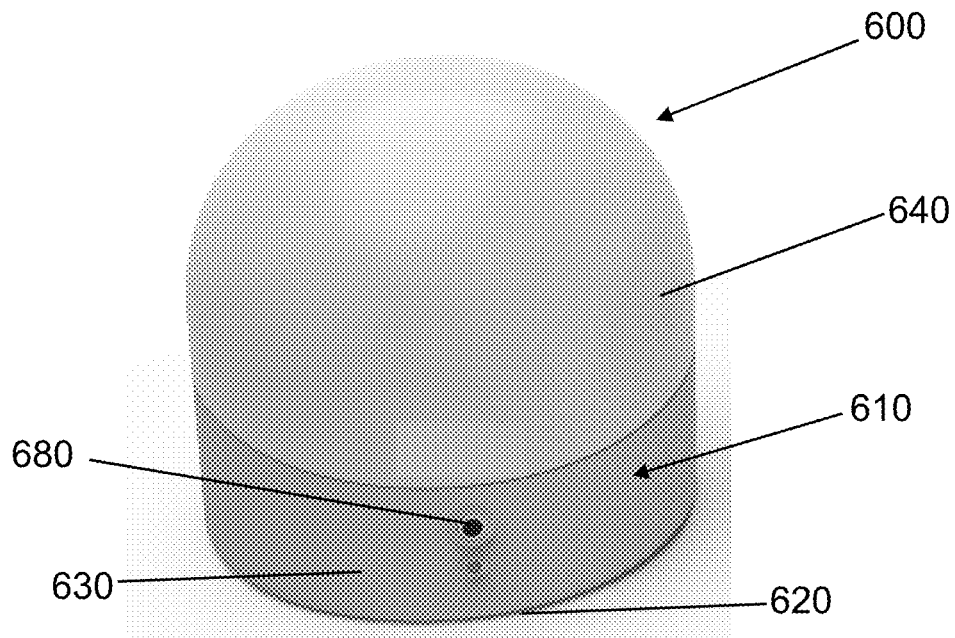
FIG. 5 is perspective view of a condiment sterilizer in a closed configuration, according to an embodiment.

FIG. 4 is a schematic view illustrating components in an internal chamber C of a condiment sterilizer ("sterilizer") in which condiment containers 501 are disposed, according to an embodiment.

Referring to FIG. 4, the chamber C is formed as a space bounded by a bottom wall (e.g., a floor of a base of the sterilizer) of the sterilizer, side walls of the sterilizer, and a top wall (e.g., a wall of a lid of the sterilizer) of the sterilizer. The sterilizer can include a first UV light assembly 520 disposed on the bottom wall of the sterilizer and including a plurality of UV light devices configured to emit light into the chamber C, and a second UV light assembly 570 disposed on a central divider in the chamber C and including a plurality of light devices configured to emit UV light laterally into the chamber C in multiple directions. The first and second UV light assemblies 520 and 570 can include UV-C LEDs or low-wave UV light devices that are not harmful to human skin.

A first reflective surface 535 (e.g., mirror) can be disposed on each of the side walls of the sterilizer. A second reflective surface (e.g., mirror) 545 can be disposed on the top wall of the sterilizer. The first and second reflective surfaces 535 and 545 can be configured to reflect UV light incident thereon toward the chamber C to increase the efficiency and efficacy of sterilizing the condiment containers 501.

FIGS. 5-9 illustrate a condiment sterilizer ("sterilizer") 600, according to an embodiment.

Figure 9:
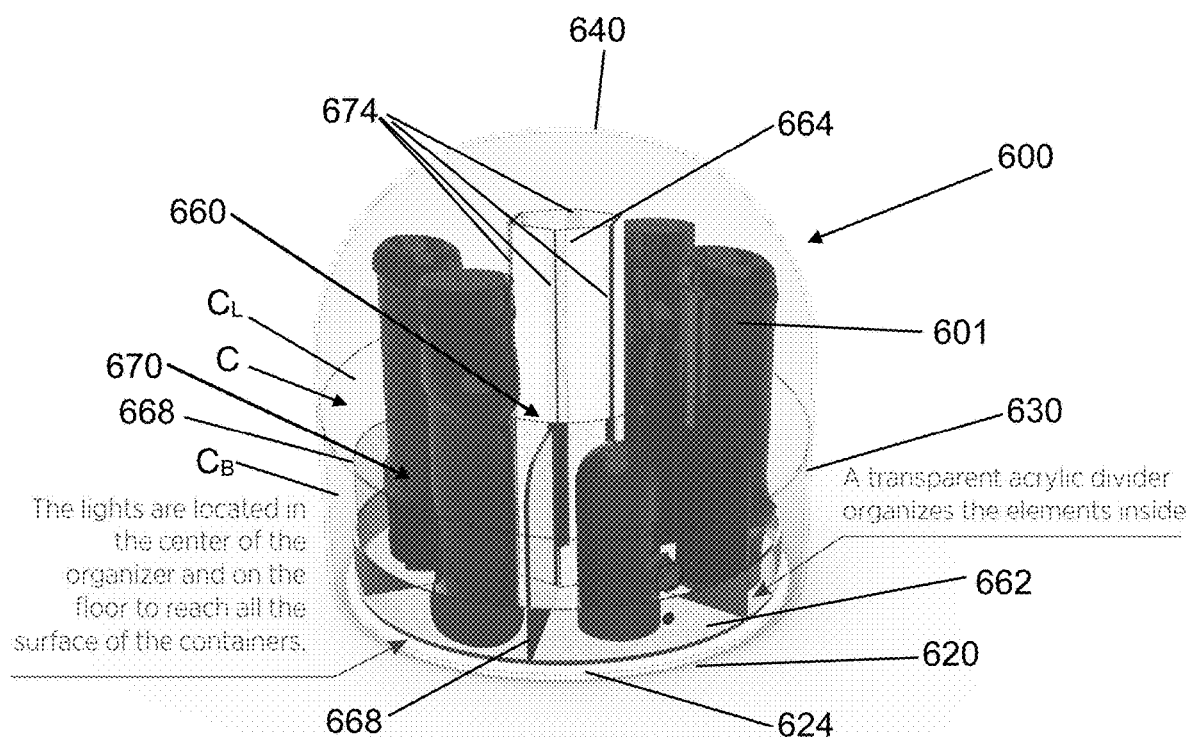
FIG. 9 is a perspective view illustrating an internal chamber of the condiment sterilizer of FIG. 5.

As shown in FIGS. 5-9, the condiment sterilizer 600 includes a base 610 and lid 640 attached to the base 610. For example, the lid 640 can be attached to the base 610 by a hinge connection and can be configured to pivot from a closed position (shown in FIGS. 5 and 9) to an open position (FIGS. 6-8), and vice-versa. As shown in FIG. 9, when the lid 640 is in the closed position, the base 610 and the lid 640 define a chamber C inside the base 610 and the lid 640. The base 610 defines a lower portion CB of the chamber C and the lid 640 defines an upper portion CL of the chamber C.

In some embodiments, the base 610 can have a cylindrical shape with a disc-shaped bottom wall 620 and a cylindrical side wall 630, and the lid 640 can have a dome shape. However, the shapes of the base 610 and the lid 640 described and illustrated herein are merely examples, and other shapes are possible.

Referring to FIGS. 6-9, the condiment sterilizer 600 includes a condiment tray 660 mounted in the base 610 (e.g., the lower portion CB of the chamber C). The condiment tray 660 can have a disc-shaped bottom platform 662, a center column or divider 664 extending vertically from the bottom platform 662, and a plurality of radial dividers 668 mounted on the center column 664 at respective radial positions on the center column 664. The center column 664 can be a hollow cylindrical member. The radial dividers 668 extend vertically along the center column 664 and radially along the bottom platform 662. Condiment compartments 670 are defined between adjacent radial dividers 668 and can accommodate condiment containers 601 of various shapes and sizes.

Figure 6:
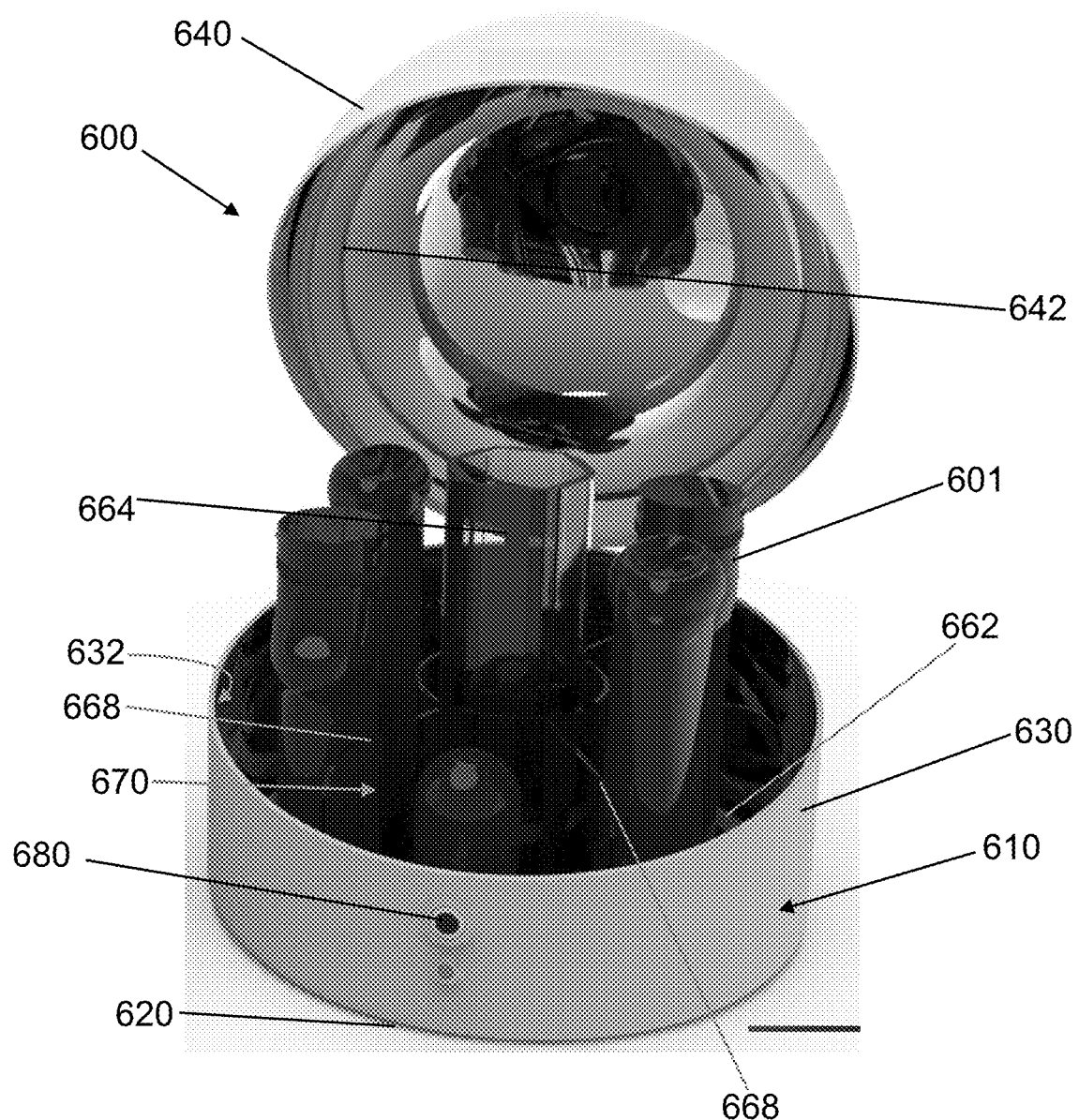
FIG. 6-8 are perspective views of the condiment sterilizer of FIG. 5 in an open configuration.
Figure 7:
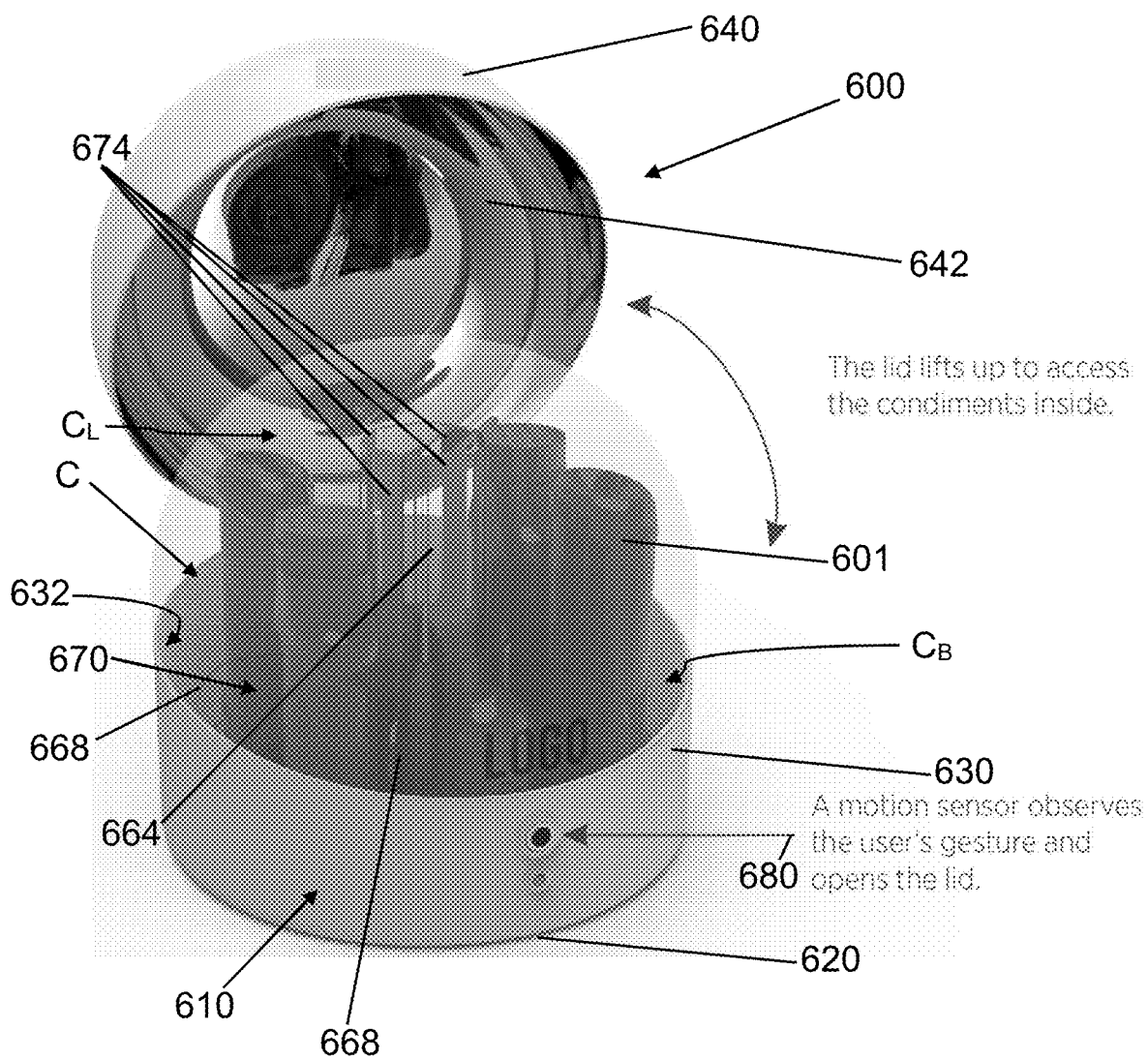
Figure 8:
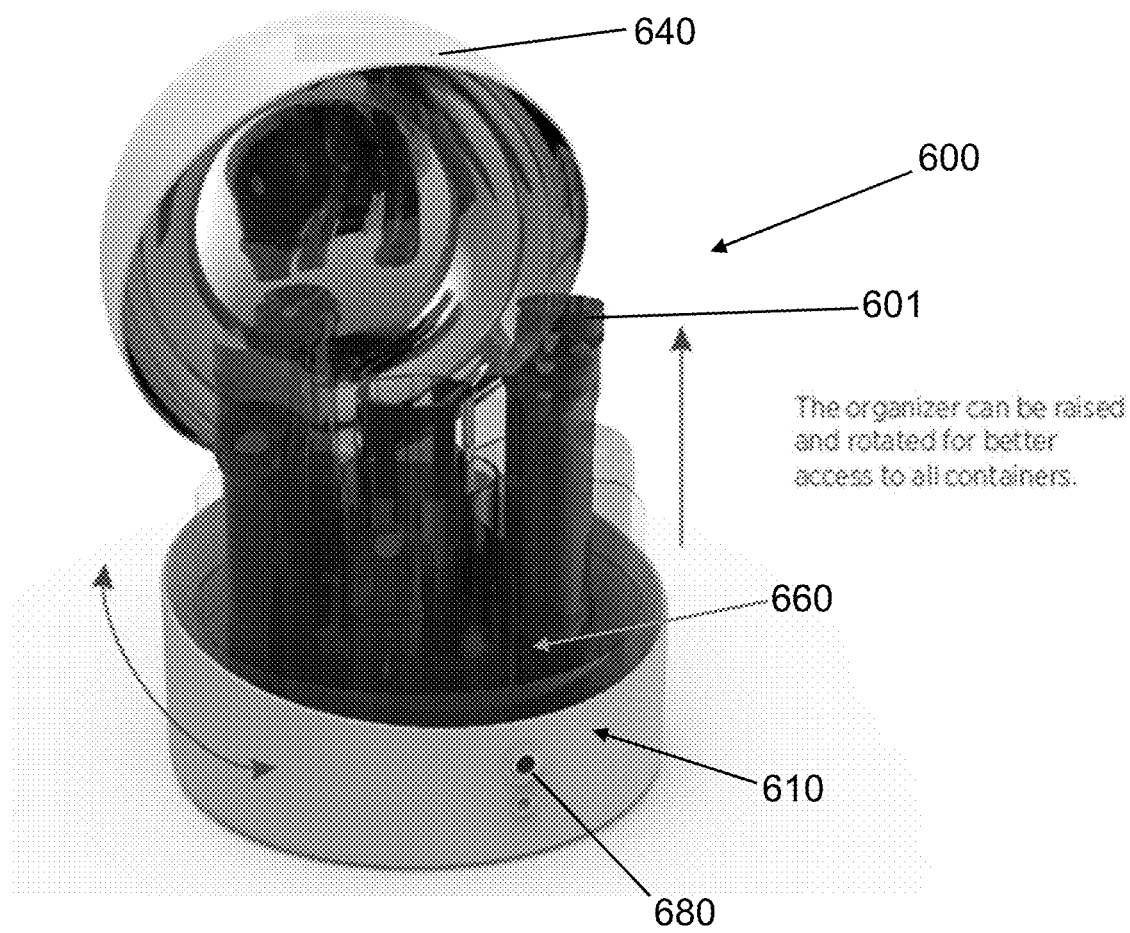

As shown in FIGS. 6 and 7, a first reflective surface 632 can be disposed on an inner surface of the cylindrical side wall 630. A second reflective surface 642 can be disposed on an inner surface of the lid 640. The first and second reflective surfaces 632 and 642 can each be formed by a reflective coating, a sheet of reflective material, or a mirror.

Referring to FIGS. 7 and 9, a first plurality of light devices 624 can be disposed on the bottom wall 620 of the base 610, and can be configured to emit UV light into the chamber C to sterilize the condiment containers 601. A second plurality of light devices 674 can be disposed on the center column 664, and can be configured to emit UV light into the chamber C. For example, the second plurality of light devices 674 can be disposed on light strips that are attached to the center column 664 at multiple locations spaced apart along a circumference of the center column 664. The first and second reflective surfaces 632 and 642 can be configured to reflect incident UV light from the first and second pluralities of light devices 624 and 674 into the chamber C to increase the efficiency and efficacy of sterilization of the condiment containers 601.

In some embodiments, the first and second pluralities of light devices 624 and 674 can include UV-C LEDs. In some embodiments, the first and second pluralities of light devices 624 and 674 can include low wave UV light devices that are not harmful to human skin. In some embodiments, the first and second pluralities of light devices 624 and 674 can include individual lighting elements. In some embodiments, the first and second pluralities of light devices 624 and 674 can include UV light strips.

As shown in FIG. 9, in some embodiments, the condiment tray 660 (including each of the bottom platform 662, the center column 664, and the plurality of radial dividers 668) can be made of a UV-transmissive (e.g., translucent or transparent) material. Thus, the condiment tray 660 enables emitted and reflected UV light to pass therethrough to promote more efficient and effective sterilization of the condiment containers. That is, due to the locations of the first and second pluralities of light devices 624 and 674, the locations of the first and second reflective surfaces 632 and 642, and the UV-transmissive material of the condiment tray 660, it is possible to efficiently sterilize all surfaces of the condiment containers 601.

Referring to FIGS. 5-8, a sensor 680, such as a motion sensor or a heat sensor, can be disposed on the outside of the base 610, so that when a patron wants condiments, the patron passes their hand or another object by the sensor 680 to initiate condiment container delivery. This helps minimize the sterilizer itself becoming covered with pathogens. When the condiment container delivery is initiated, a controller (e.g., the controller 190 described above with respect to FIG. 1) of the sterilizer checks to ensure that the first and second pluralities of light devices 624 and 674 are off, then lid 640 of the sterilizer pivots open and the condiment tray 660 rises in the base 610 to present the condiment containers 601 to the patron. When the patron has finished using a condiment container 601, the condiment container 601 is placed back on the condiment tray 660 and the condiment tray 660 descends in the base 610. The first and second pluralities of light devices 624 and 674 are then turned on for a predetermined period of time to sanitize the condiment containers 601.

In some embodiments, the patron causes the condiment tray 660 and condiment containers 601 to descend back into the chamber C and the lid 640 to close by passing their hand in front of the sensor 680 once again. In some embodiments, the weight of a condiment container 601 being returned to the condiment tray 660 is sensed by a weight sensor in communication with the controller in order for the condiments to retreat back into the chamber C, e.g., by a slight voltage spike as the drive motors work to keep the condiment tray 660 in a given position. For example, a dedicated weight sensor (e.g., the weight sensor 192 described above) can be provided on the top of the condiment tray 660. The dedicated weight sensor can be operably connected to the controller, and disposed on the condiment tray 660 and configured to measure a weight applied to the condiment tray 660.

In some embodiments, the condiment sterilizer 600 can include (in addition to or instead of the sensor 680) an electronic button that is electrically connected to the controller, and the patron can press the button to either cause the lid 640 to open and the condiment tray 660 to move up, or cause the lid 640 to close and the condiment tray 660 to move down and then turn on the first and second pluralities of light devices 624 and 674 for a predetermined period of time to sanitize the condiment containers 601.

In some embodiments, when the lid 640 is open and the condiment tray 660 is raised up, the controller can cause the lid 640 to close and the condiment tray 660 to move down and then turn on the first and second pluralities of light devices 624 and 674 for a predetermined period of time, in response to the sensor 680 not sensing the presence or movement of the patron's hand or other object after a threshold amount of time has elapsed.

Various mechanisms can be used to cause the lid 640 to swing open and closed. For example, in some embodiments, the lid 640 can have arcuate toothed arms that are driven by a pinion gear attached to the output shaft of an electric motor housed within the chamber C. Various mechanisms can also be used to cause the condiment tray 660 to rise and descend in the lower portion CB of the chamber C. For example, electric motor-driven jack screws can be mounted to the condiment tray 660 to move the condiment tray 660 up and down. Alternatively, electric motor-driven drive wheels (i.e., pinion gears) attached to the condiment tray 660 can engage with toothed tracks located along the walls of the chamber C to move the condiment tray 660 up and down.

Although not shown in FIGS. 5-9, the condiment sterilizer 600 can further include the power-storage devices 194, the recharging circuitry 196, the charging port 197, the center contact 198*a*, and the ring-shaped contact 198*b* described above with respect to FIG. 1.

FIGS. 10-13 illustrate a condiment sterilizer ("sterilizer") 1000, according to an embodiment.

Referring to FIGS. 10-13, the sterilizer 1000 includes a base 1100, a lid 1200, an inner tub 1300, and a condiment tray 1600. The base 1100 can have a cylindrical shape with a disc-shaped bottom wall 1120 and a cylindrical side wall 1130, and the lid 1200 can have a dome shape. However, the shapes of the base 1100 and the lid 1200 described and illustrated herein are merely examples, and other shapes are possible. The lid 1200 can be pivotally attached to the base 1100 by a pivot connection between pivot arms 1210 of the lid 1200 and a pivot mount 1132 on the side wall 1130 of the base 1100.

A sensor 1080 can be disposed on the outside of the base 1100. The sensor 1080 can be a motion sensor or a heat (e.g., IR) sensor that is configured to detect motion or proximity of a person's hand, or another object, and can been implemented to control functions of the sterilizer 1000, as described later in more detail.

Figure 11:
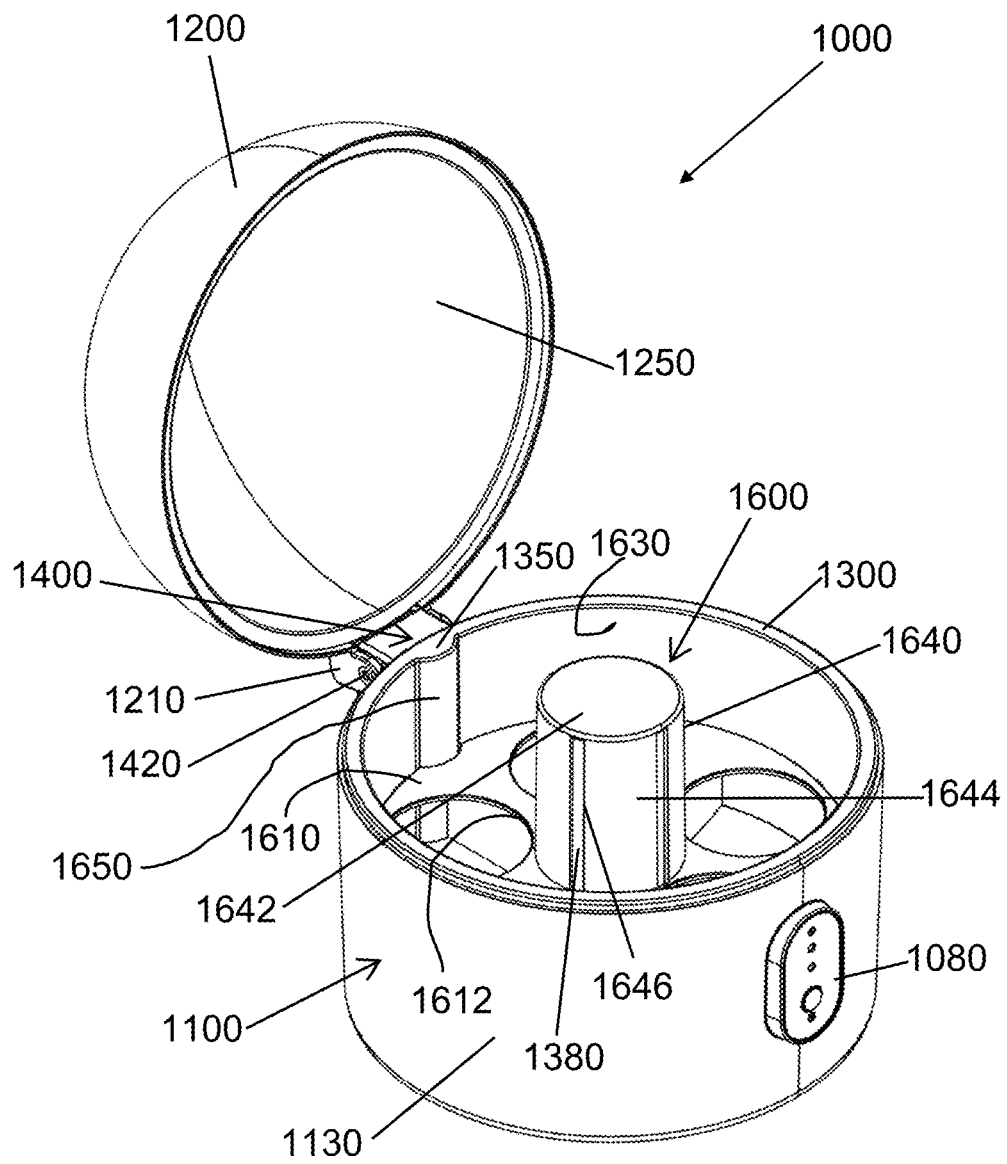
FIG. 11 is perspective view of the condiment sterilizer of FIG. 10 a closed configuration, according to an embodiment.
Figure 12:
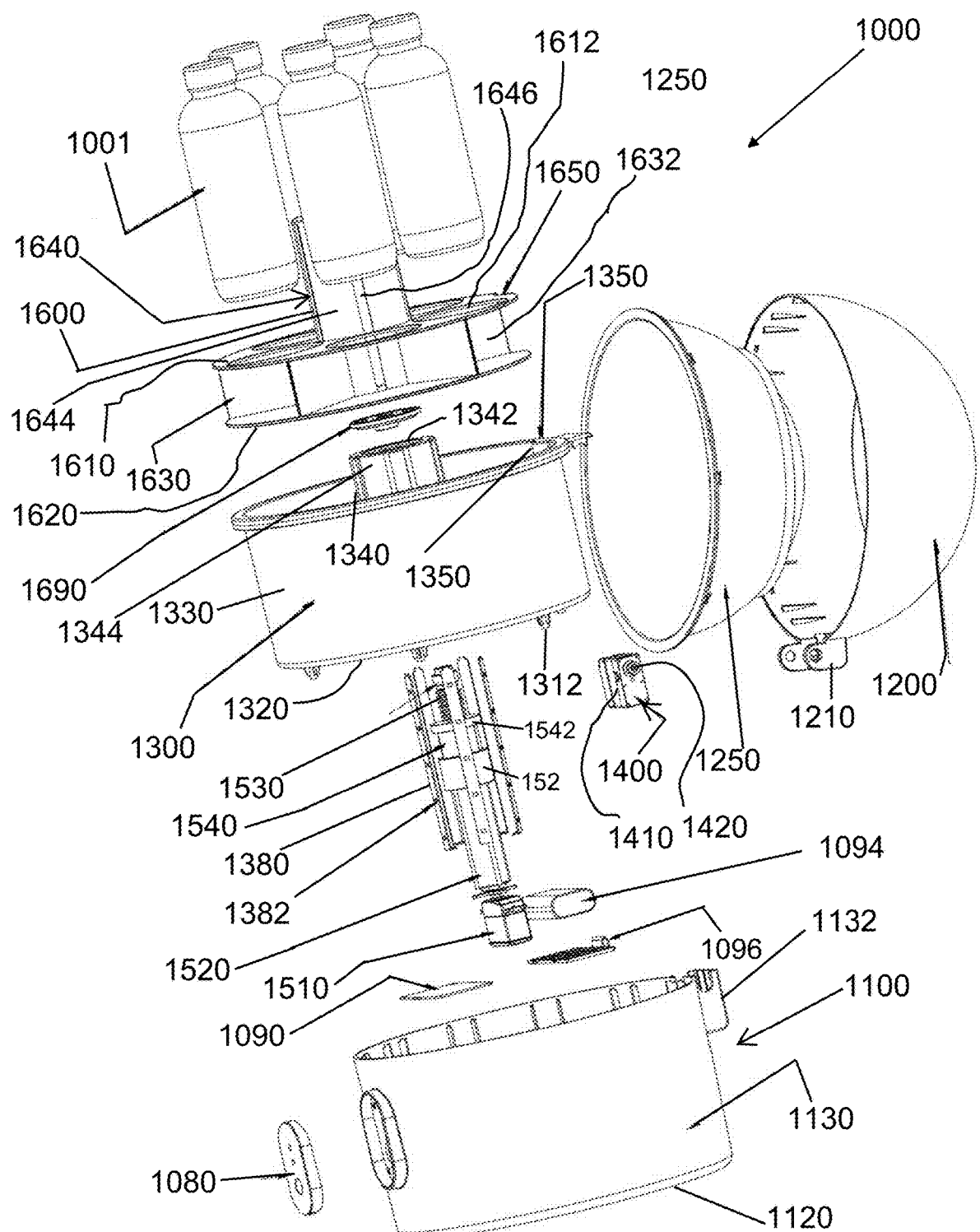
FIG. 12 is an exploded view of the condiment sterilizer of FIG. 10, according to an embodiment.
Figure 13:
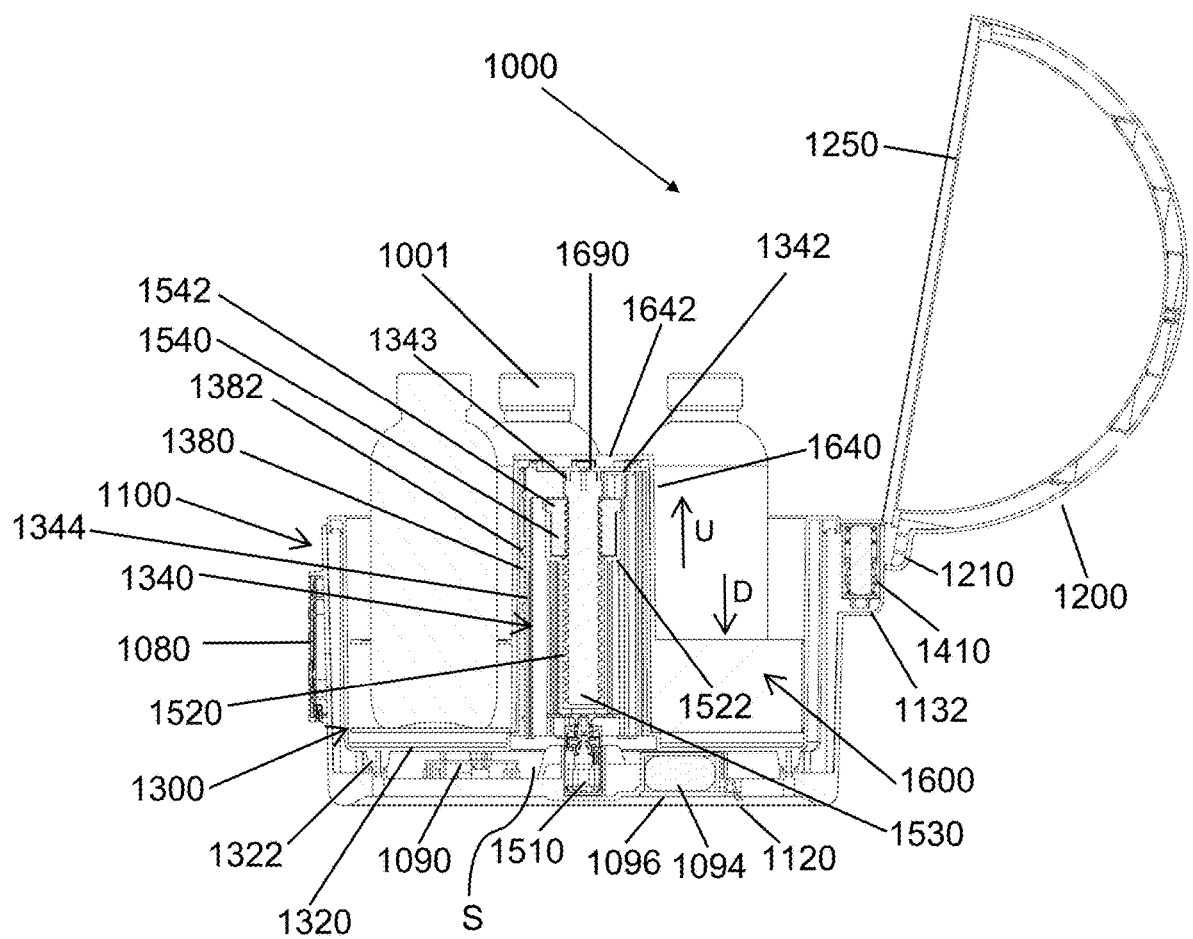
FIG. 13 is a cross-sectional view of the condiment sterilizer of FIG. 10, according to an embodiment.

The inner tub 1300 is disposed in the base 1100. The inner tub 1300 can have a cylindrical shape with a disc-shaped bottom wall 1320, a cylindrical side wall 1330, and a hollow center column 1340 having a top wall 1342 and a side wall 1344. Legs 1322 can be disposed on the bottom wall 1320. As shown in FIG. 13, the legs 1322 can support the inner tub 1300 on the bottom wall 1120 of the base 1100 such that a space S for accommodating electronic components is formed between bottom wall 1320 of the inner tub 1300 and the bottom wall 1120 of the base 1100. As shown in FIGS. 11 and 12, the inner tub 1300 can further include a guide rail 1350 disposed on the side wall 1344 for guiding vertical movement of the condiment tray 1600.

The lid 1200 can be configured to pivot from a closed position (shown in FIG. 10) to an open position (shown in FIG. 11), and vice-versa. When the lid 1200 is in the closed position, the base 1100, the lid 1200, and the inner tub 1300 define a chamber inside the base 1100/inner tub 1300 and the lid 1200. The base 1100 defines a lower portion of the chamber and the lid 1200 defines an upper portion of the chamber.

A plurality of UV light strips 1380 can be mounted on the side wall 1344 of the center column 1340 at positions around of the center column 1340. Each UV light strip 1380 includes one or more UV light devices 1382 configured to emit UV light into the chamber of the sterilizer 1000 to sterilize condiment containers 1001. In some embodiments, the light devices 1382 can include UV-C LEDs. In some embodiments, the light devices 1382 can be low wave UV light devices that are not harmful to human skin.

An inner cover 1250 can be disposed over an inner surface of the lid 1200. In some embodiments, the inner cover 1250 can be made of a reflective material that can reflect UV light incident thereon toward the chamber to increase sterilizing efficacy and efficiency.

The condiment tray 1600 is mounted in the base 1100 and disposed inside the inner tub 1300. The condiment tray 1600 can have a disc-shaped top platform 1610, a disc-shaped bottom platform 1620 vertically spaced from the top platform 1610, a plurality of radial dividers 1630 disposed between the top platform 1610 and the bottom platform 1620 and spaced apart from each other along the top platform 1610 and the bottom platform 1620, and a hollow center column 1640. Compartments 1632 for accommodating the condiment containers 1001 are formed around the hollow center column 1640, between adjacent radial dividers 1630. The top platform 1610 includes a plurality of holes 1612 respectively aligned with and opening into the compartments 1632, such that the condiment containers 1001 can be inserted into the compartments 1632 through the holes 1612.

Referring to FIGS. 11 and 12, the condiment tray 1600 can further include a guide channel 1650 that receives the guide rail 1350. The guide rail 1350 engages the guide channel 1650 and prevents the condiment tray 1600 from rotating about its central axis as the condiment tray 1600 moves up or down in the base 1100/inner tub 1300.

The center column 1640 of the condiment tray 1600 includes a top wall 1642, a side wall 1644. The side wall 1644 can include a plurality of open slots 1646 disposed at positions spaced apart around the side wall 1644.

Figure 10:
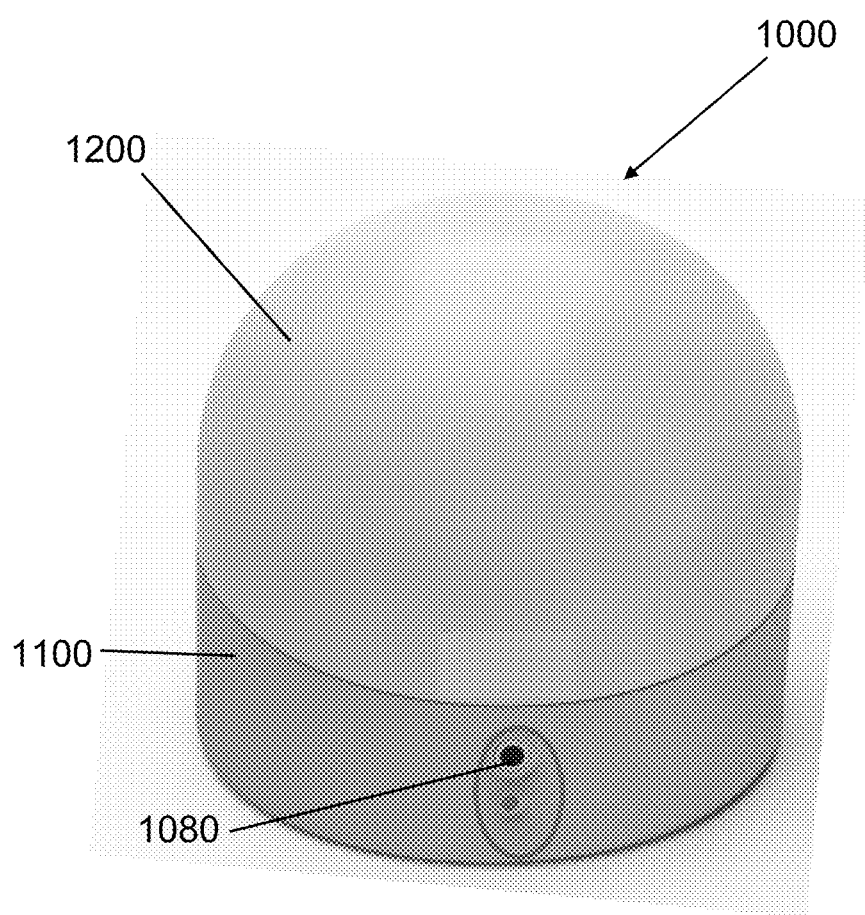
FIG. 10 is perspective view of a condiment sterilizer in a closed configuration, according to an embodiment.

As shown in FIGS. 10 and 13, the center column 1640 of the condiment tray 1600 is disposed over and coaxially aligned with the center column 1340 of the inner tub 1300. As will be described in more detail later, when the condiment tray 1600 is in its lowest position (i.e., a minimum height described below) in the base 1100/inner tub 1300 (corresponding to a configuration in which the lid 1200 can be closed and the sterilizer 1000 can be operated to sanitize the condiment containers 1001) the center column 1640 of the condiment tray 1600 covers the center column 1340 of the inner tub 1300, and the light strip 1380 and UV light devices 1382 are aligned with respective open slots 1646.

Thus, the respective open slots 1646 expose the UV light devices 1382 to the space of the chamber in the sterilizer 1000 such that the UV light devices 1382 can emit UV light into the chamber unobstructed by the center column 1640 of the condiment tray 1600. Thus, the configuration of the open slots 1646 and the light strip 1380/UV light devices 1382 enables the condiment tray 1600 to be made of a material of low UV transmissivity without preventing the UV light devices 1382 from emitting UV light into the chamber of the base 1100/inner tub 1300.

In some embodiments, the condiment tray 1600 can be made of a UV-transmissive (e.g., transparent or translucent) material, so that UV light can pass therethrough to promote efficient and thorough sanitization of the condiment containers 1001.

The sterilizer 1000 further includes a lid drive assembly 1400. As shown in FIGS. 11 and 12, the lid drive assembly 1400 includes lid motor 1410 and a pivot shaft 1420 configured to be rotated in opposite directions by the lid motor 1410 pivot the lid 1200 from an open position to a closed position, and vice-versa. The lid motor 1410 can be accommodated in the pivot mount 1132 of the base 1100. The pivot shaft 1420 is received in the pivot arms 1210 of the lid 1200 and the pivot mount 1132. The pivot shaft 1420 can be further retained by a retaining arm 1332 on the side wall 1330 of the inner tub 1300.

The sterilizer 1000 is configured to raise the condiment tray 1600 to a maximum height at which the condiment containers 1001 can be retrieved by a patron for use, and lower the condiment tray 1600 to a minimum height at which the condiment containers 1001 can be stored and sterilized in the sterilizer 1000. More specifically, the sterilizer 1000 includes lift assembly 1500 mounted in the base 1100 for raising and lowering the condiment tray 1600 in the base 1100/inner tub 1300. The lift assembly 1500 includes a lift motor 1510 mounted to the base 1100, an internally threaded lead screw sleeve 1520 connected to the lift motor 1510 and configured to be rotated in opposite directions by the lift motor 1510, an externally threaded lead screw 1530 received in the lead screw sleeve 1520, and a stopper 1540 fixed to the lead screw 1530 and received in the lead screw sleeve 1520. The lift motor 1510 can be disposed in the space S between the bottom wall 1120 of the base 1100 and the bottom wall 1320 of the inner tub 1300. The lead screw sleeve 1520, the lead screw 1530, and the stopper 1540 are accommodated inside the center column 1340 of the inner tub 1300. Thus, the inner tub 1300 is mounted over and covers the lift assembly 1500 inside the base 1100. The lead screw 1530 extends through an opening 1343 in the top wall 1342 of the inner tub 1300, and a top end of the lead screw 1530 is connected to the condiment tray 1600. More specifically, the top end of the lead screw 1530 is connected the underside of the top wall 1642 of the condiment tray 1600 by a screw connector 1690, as shown in FIGS. 12 and 13.

When the lift motor 1510 is operated, the lead screw sleeve 1520 rotates relative to the lead screw 1530, which causes the lead screw 1530 to move up in the direction U in FIG. 13 or down in the direction D in FIG. 13, (depending on the direction in which the lead screw sleeve 1520 rotates) relative to the lead screw sleeve 1520 in the base 1100/inner tub 1300. The condiment tray 1600 moves up (direction U) or down (direction D), e.g., raises or lowers, in the base 1100/inner tub 1300 corresponding to the movement of the lead screw 1530. For example, the lift motor 1510 can rotate the lead screw sleeve 1520 in a first direction relative to the lead screw 1530 and thereby cause the lead screw 1530 to move up and raise the condiment tray 1600 in the base 1100/inner tub 1300. For example, the lift motor 1510 can rotate the lead screw sleeve 1520 in a second direction relative to the lead screw 1530 and thereby cause the lead screw 1530 to move down and lower the condiment tray 1600 in the base 1100/inner tub 1300.

The stopper 1540 rotates together with the lead screw 1530 and limits upward and downward movement of the condiment tray 1600. More specifically, upward movement of the condiment tray 1600 is limited/stopped by an upper flange 1542 of the stopper contacting an underside of the top wall 1342 of the center column 1340 of the inner tub 1300, and downward movement of the condiment tray 1600 is limited/stopped by a lower end of the stopper 1540 contacting an inner ledge 1522 (see FIG. 13) of the lead screw sleeve 1520. Thus, the center column 1340 of the inner tub 1300 and the stopper 1540 limit upward travel of the condiment tray 1600 to the maximum height at which the condiment containers 1001 are presented for retrieval by a patron, and the lead screw sleeve 1520 and the stopper 1540 limit downward travel of the condiment tray 1600 to the minimum height at which the condiment containers 1001 are stored in the sterilizer 1000 to be sterilized by operation of the UV light devices 1382.

As the condiment tray 1600 moves up or down, the guide rail 1350 of the inner tub 1300 and the guide channel 1650 of the condiment tray 1600 engage each other and prevent the condiment tray 1600 from rotating.

As shown in FIGS. 12 and 13, a controller 1090 and a battery 1094 can be disposed in the space S between the bottom wall 1120 of the base 1100 and the bottom wall 1320 of the inner tub 1300. A battery cover 1096 can also be provided in the space S to cover and protect the battery 1094.

The controller 1090 is electrically connected to the sensor 1080, the lid motor 1410, the lift motor 1510, and the light devices 1382. The controller 1090 can be configured to control operations of the lid motor 1410 and the lift motor 1510 (e.g., rotation and rotational direction of the lid motor 1410 and the lift motor 1510) based on signals received from the sensor 1080. The battery 1094 is electrically connected to the sensor 1080, the lid motor 1410, and the lift motor 1510 to supply power thereto. Although the sterilizer 1000 is described as including the battery 1094, in some embodiments, the battery 1094 can be supplemented or replaced by an AC power source, for example. Additionally, although not shown in FIGS. 10-13, the sterilizer 1000 can further include the recharging circuitry 196, the charging port 197, the center contact 198*a*, the ring-shaped contact 198*b*, and/or the weight sensor 192 described above with respect to FIG. 1.

Example operations of the sterilizer 1000 are described below.

When a patron wants condiments, the patron passes their hand or an object by the sensor 1080 to initiate delivery of a condiment container 1001. This helps minimize the sterilizer 1000 itself becoming covered with pathogens. When the controller 1090 receives a signal from the sensor 1080 indicating presence or movement of the patron's hand or object while the lid 1200 is closed, the controller 1090 checks to ensure that the plurality of light devices 1382 are off, and then controls the lid motor 1410 to pivot the lid 1200 open, and controls the lift motor 1510 to cause the condiment tray 1600 to move up in the base 1100/inner tub 1300 to its highest position (e.g., the maximum height described above) to present the condiment containers 1001 to the patron for retrieval and use.

When the patron has finished using a condiment container 1001 after removing the condiment container 1001 from the condiment tray 1600, the condiment container 1001 is placed back on the condiment tray 1600. The controller 1090 can then control the lift motor 1510 to cause the condiment tray 1600 to move down in the base 1100/inner tub 1300 into its lowest position (e.g., the minimum height described above) for sterilizing the condiment containers 1001, and control the lid motor 1410 to cause the lid 1200 to close while or after the condiment tray 1600 moves down in the base 1100/inner tub 1300. The, upon confirming that the lid 1200 is closed, controller 1090 can turn on the light devices 1382 for a predetermined period of time to sanitize the condiment containers 1001.

In some embodiments, the controller 1090 can cause the condiment tray 1600 to move down in the base 1100/inner tub 1300 into its lowest position in response to a weight sensor (e.g., the weight sensor 192 of FIG. 1) that is connected to the controller 1090 sensing the weight of a condiment container 1001 being returned to the condiment tray 1600 after the lid 1200 has been opened.

In some embodiments, the sterilizer 1000 can include (in addition to or instead of the sensor 1080) an electronic button that is electrically connected to the controller 1090, and the patron can press the button to either cause the lid 1200 to open and the condiment tray 1600 to move up, or cause the lid 1200 to close and the condiment tray 1600 to move down and then turn on the light devices 1392 for a predetermined period of time to sanitize the condiment containers 1001.

In some embodiments, when the lid 1200 is open and the condiment tray 1600 is raised up, the controller 1090 can cause the lid 1200 to close and the condiment tray 1600 to move down and then turn on the light devices 1382 for a predetermined period of time, in response to the sensor 1080 not sensing the presence or movement of the patron's hand or other object after a threshold amount of time has elapsed.

Reference in this specification to "embodiments" (e.g., "some embodiments," "various embodiments," "one embodiment," "an embodiment," etc.) means that a particular feature, structure, or characteristic described in connection with the embodiment is included in at least one embodiment of the disclosure. The appearances of these phrases in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "includes" and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

Although the subject matter has been described in language specific to structural features and/or methodological acts, it is to be understood that the subject matter defined in the appended claims is not necessarily limited to the specific features or acts described above. Specific embodiments have been described herein for purposes of illustration, but various modifications can be made without deviating from the scope of the embodiments. The specific features and acts described above are disclosed as example forms of implementing the claims that follow. Accordingly, the embodiments are not limited except as by the appended claims.

We claim:

1. A condiment sterilizer, comprising:
   a base;
   a lid attached to the base and configured to move between an open position and a closed position, the base and the lid defining an internal chamber when the lid is in the closed position;
   a condiment tray mounted in the base and including:
      a center column, and
      one or more compartments disposed around the center column and configured to accommodate one or more condiment containers; and
   at least one UV light device disposed on the center column and configured to emit UV light into the internal chamber.

2. The condiment sterilizer of claim 1, wherein the condiment tray is made of a UV-transmissive material.

3. The condiment sterilizer of claim 1, further comprising a reflective surface disposed on either one or both of the base and the lid.

4. The condiment sterilizer of claim 1, wherein the at least one UV light device includes a plurality of UV light devices disposed on light strips that are attached to the center column at multiple locations spaced apart along a circumference of the center column.

5. The condiment sterilizer of claim 1, further comprising:
a sensor configured to sense heat or motion; and
a controller connected to the sensor and configured to cause the lid to move from the closed position to the open position in response to the sensor sensing the heat or the motion.

6. The condiment sterilizer of claim 5, wherein the controller is further configured to cause the condiment tray to move up in the base in response to the sensor sensing the heat or the motion.

7. The condiment sterilizer of claim 6, wherein the controller is further configured to cause the lid to move back to the closed position, cause the condiment tray to move down in the base, and turn on the at least one UV light device, in response to sensing a condiment container among the one more condiment containers being returned to the condiment tray.

8. The condiment sterilizer of claim 5, wherein the controller is further configured to cause the lid to move back to the closed position, and turn on the at least one UV light device, in response to sensing a condiment container among the one more condiment containers being returned to the condiment tray.

9. The condiment sterilizer of claim 1, further comprising at least one additional UV light device disposed on a bottom wall or a side wall of the base.

10. A condiment sterilizer, comprising:
a base;
a lid attached to the base and configured to move between an open position and a closed position;
an inner tub disposed in the base, wherein the inner tub includes a first hollow center column, and the inner tub and the lid define an internal chamber when the lid is in the closed position;
a condiment tray mounted over the inner tub in the internal chamber, wherein the condiment tray includes a second hollow center column disposed over the first hollow center column, and one or more compartments disposed around the second hollow center column and configured to accommodate one or more condiment containers;
a lift assembly mounted in the base and configured to raise and lower the condiment tray in the inner chamber, wherein the inner tub covers the lift assembly; and
at least one UV light device configured to emit UV light into the internal chamber.

11. The condiment sterilizer of claim 10, wherein the lift assembly comprises:
a lead screw sleeve disposed in the first hollow center column;
a lead screw disposed in the lead screw sleeve, the lead screw extending through an opening in a top wall of the first hollow center column and having a top end connected to the condiment tray; and
a lift motor configured to:
rotate the lead screw sleeve in a first direction relative to the lead screw and thereby cause the lead screw to move up and raise the condiment tray in the internal chamber, and
rotate the lead screw sleeve in a second direction relative to the lead screw and thereby cause the lead screw to move down and lower the condiment tray in the internal chamber.

12. The condiment sterilizer of claim 11, wherein the lift assembly further comprises a stopper fixed to the lead screw, and
wherein the stopper is configured to:
engage the top wall of the first hollow center column to limit upward travel of the condiment tray to a maximum height, and
engage a ledge of the lead screw sleeve to limit downward travel of the condiment tray to a minimum height.

13. The condiment sterilizer of claim 11, further comprising:
a guide rail disposed on a side wall of the inner tub; and
a guide channel disposed on a side wall of the condiment tray,
wherein the guide rail and the guide channel are configured to engage each other to limit or prevent rotation of the condiment tray when the condiment tray is raised or lowered.

14. The condiment sterilizer of claim 10, wherein:
the at least one UV light device includes one or more UV light devices disposed on the first hollow center column,
the second hollow center column includes one or more open slots, and
when the condiment tray is disposed at a minimum height in the internal chamber, the second hollow center column covers the first hollow center column and the one or more UV light devices are exposed to the internal chamber by the one or more open slots.

15. The condiment sterilizer of claim 10, further comprising:
a sensor configured to sense heat or motion; and
a controller connected to the sensor and configured to control a motor of the lift assembly to raise the condiment tray in the internal chamber in response to the sensor sensing the heat or the motion.

16. The condiment sterilizer of claim 15, further comprising a lid drive assembly configured to move the lid,
wherein the controller is further configured to cause the lid drive assembly to move the lid from the closed position to an open position in response to the sensor sensing the heat or the motion.

17. The condiment sterilizer of claim 16, wherein the controller is further configured to control the motor of the lift assembly to lower the condiment tray in the internal chamber, cause the lid drive assembly to move the lid back to the closed position, and turn on the at least one UV light device, in response to sensing a condiment container among the one more condiment containers being returned to the condiment tray.

18. The condiment sterilizer of claim 15, wherein the controller is further configured to control the motor of the lift assembly to lower the condiment tray in the internal chamber, and turn on the at least one UV light device, in response to sensing a condiment container among the one more condiment containers being returned to the condiment tray.

19. The condiment sterilizer of claim 10, wherein the inner tub further includes a plurality of legs disposed on a bottom wall of the inner tub, and
wherein the plurality of legs support the inner tub on a bottom wall of the base such that a space for accommodating electronic components is formed between bottom wall of the inner tub and the bottom wall of the base.

\* \* \* \* \*